(12) United States Patent
Bernhard et al.

(10) Patent No.: US 11,249,024 B2
(45) Date of Patent: Feb. 15, 2022

(54) OPTICAL MEASURING SYSTEM AND METHOD COMPRISING THE SAME

(71) Applicant: Endress+Hauser Conducta GmbH+Co. KG, Gerlingen (DE)

(72) Inventors: Ralf Bernhard, Stuttgart (DE); Manfred Jagiella, Notzingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 23 days.

(21) Appl. No.: 16/558,621

(22) Filed: Sep. 3, 2019

(65) Prior Publication Data

US 2020/0072751 A1  Mar. 5, 2020

(30) Foreign Application Priority Data

Sep. 4, 2018 (DE) ...................... 10 2018 121 534.7

(51) Int. Cl.
*G01N 21/64* (2006.01)
*G01N 33/18* (2006.01)

(52) U.S. Cl.
CPC ....... *G01N 21/645* (2013.01); *G01N 33/1833* (2013.01); *G01N 2021/6463* (2013.01); *G01N 2201/062* (2013.01); *G01N 2201/06113* (2013.01)

(58) Field of Classification Search
CPC ....... G01N 2201/06113; G01N 21/645; G01N 2021/6463; G01N 33/1833
See application file for complete search history.

(56) References Cited

U.S. PATENT DOCUMENTS

2012/0170023 A1\* 7/2012 Szobota ............... G01N 21/552
356/51

\* cited by examiner

*Primary Examiner* — David P Porta
*Assistant Examiner* — Fani Boosalis
(74) *Attorney, Agent, or Firm* — Christopher R. Powers; Endress+Hauser (USA) Holding Inc.

(57) ABSTRACT

The present disclosure includes an optical measuring system having at least one light source that radiates excitation light into a medium to be measured. The excitation light is converted into fluorescent light by the medium. The optical measuring system also includes a first photodiode that receives a decay curve of the fluorescent light and converts it into a first signal and at least one optical component that receives the fluorescent light and converts it into a second signal. A data processing unit determines an oil-in-water content based on the first signal and the second signal.

11 Claims, 4 Drawing Sheets

OPTICAL MEASURING SYSTEM AND METHOD COMPRISING THE SAME

CROSS-REFERENCE TO RELATED APPLICATION

The present application is related to and claims the priority benefit of German Patent Application No. 10 2018 121 534.7, filed on Sep. 4, 2018, the entire contents of which are incorporated herein by reference.

TECHNICAL FIELD

The present disclosure relates to an optical measuring system and a method for determining an oil-in-water content using the optical measuring system.

BACKGROUND

The oil-in-water content can be measured, inter alia, by means of fluorescence. For this purpose, a sample is excited with short-wave radiation. Oil dispersed in the water then emits fluorescent light, which can be detected. In the simplest case, only the total intensity of the fluorescent light is measured. If the proportion of the oil capable of fluorescence is known, it is possible to determine its concentration by means of a calibration when the composition of the oil is constant. If the composition changes, a fixed calibration will lead to measurement errors.

Additional information about the oil is given in the spectral distribution of the fluorescent light, its decay time, and its dependence upon the excitation wavelength. The decay time is measured by recording time-resolved spectra. However, a very fast spectrometer is necessary for this purpose, which equates to a great outlay on equipment, with high costs.

SUMMARY

The aim of the invention is to determine the oil-in-water content by means of a cost-effective arrangement.

The aim is achieved by an optical measuring system including at least one light source that radiates excitation light into a medium to be measured, wherein the excitation light is converted into fluorescent light by the medium. The optical measuring system also includes a first photodiode that receives a decay curve of the fluorescence light and converts it into a first signal and at least one optical component that receives the fluorescent light and converts it into a second signal. A data processing unit determines an oil-in-water content based on the first signal and the second signal.

This results in a cost-effective arrangement which can determine the oil-in-water content from the first and second signals by means of a calibration model. This is possible because additional information about the oil is contained in the spectral distribution of the fluorescent light, its decay time, and its dependence upon the excitation wavelength.

"Light," within the meaning of this application, is not to be limited to the visible range of the electromagnetic spectrum but is to be understood as electromagnetic radiation of any wavelength, and also in the far ultraviolet (UV) and in the infrared (IR) wavelength ranges.

In one embodiment, further measurement values, such as temperature, pressure, turbidity, absorption, pH, conductivity, density, dielectric constant, etc., can be considered.

In one embodiment, the optical component is configured as a second photodiode, which receives a decay curve of the fluorescent light and converts it into a second signal.

In one embodiment, the first photodiode comprises a first filter for a first wavelength interval, and/or the second photodiode comprises a second filter for a second wavelength interval, wherein the second wavelength interval differs from the first wavelength interval at least in sections.

In one embodiment, the optical component is designed as a spectrometer, whose time resolution is not sufficient for determining the decay curve of the fluorescent light.

In one embodiment, the optical measuring system comprises at least two optical components, in particular, at least one second photodiode and one spectrometer.

In one embodiment, the light source is configured as at least one LED, flash lamp, or as at least one laser.

In one embodiment, the optical measuring system is configured as an immersion probe with a diameter of 20-50 mm, such as, for example, 40 mm, wherein the light source, first photodiode, optical component, and data processing unit are arranged in the immersion probe.

In one embodiment, the optical measuring system is configured as an immersion probe, wherein the immersion probe comprises a medium-contacting first section with a diameter of 12 mm and a non-medium-contacting second section with a diameter greater than or equal to 12 mm, wherein the light source, first photodiode, optical component, and data processing unit are arranged in the second section.

In one embodiment, the optical measuring system is configured as a flow-through measuring cell.

In one embodiment, the light source is arranged in a first module, and wherein the first photodiode and the optical component are arranged in a second module, wherein the first module is offset from the second module.

The aim is further achieved by a method for determining the oil-in-water content with an optical measuring system as described above, including steps of radiating excitation light into the medium to be measured, where the excitation light is converted to fluorescent light, measuring the fluorescent light with a photodiode, measuring the fluorescent light with an optical element, and determining the oil-in-water content using the measurements of the photodiode and the optical element.

BRIEF DESCRIPTION OF THE DRAWINGS

This will be explained in more detail with reference to the following figures.

DETAILED DESCRIPTION

In the figures, the same features are identified with the same reference symbols.

Figure 1:
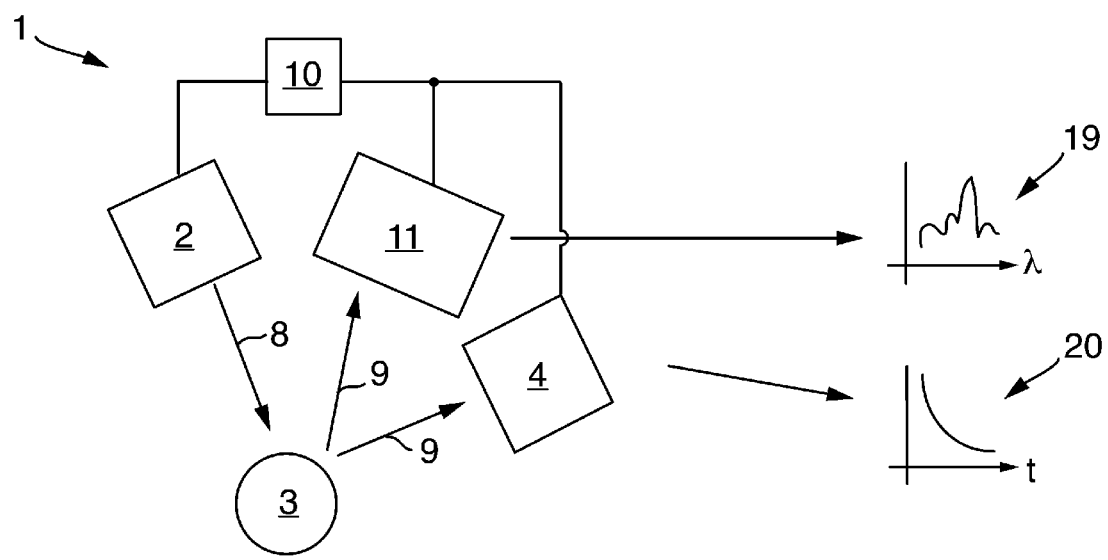
FIG. 1 shows the claimed optical measuring system in an embodiment.

FIG. 1 shows an optical measuring system 1 with a light source 2. The light source 2 radiates excitation light 8 into the medium 3 to be measured, wherein the excitation light 8 is converted into fluorescent light 9 by the medium 3. The fluorescent light 9 is received by a first photodiode 4 and converted into a first signal. The photodiode 4 measures the decay curve 20 of the fluorescent light 9. The decay time is determined via the decay curve 20. The decay time obtained is an integral value, without spectral information. The feature, "determining the decay curve," is also intended to mean the determination of the decay time by measuring the phase shift in the event of periodic excitation.

In FIG. 1, the fluorescent light 9 is also received by a spectrometer 11, which converts the fluorescent light 9 into a second signal. The time resolution of the spectrometer 11 is not sufficient for determining a decay curve of the fluorescent light 9. The spectrometer 11 measures the spectrum 19 of the fluorescent light 9. In FIG. 1, the spectrometer 11 is the second optical element, within the meaning of this application.

The light source 2, the spectrometer 11, and the photodiode 4 are connected to a data processing unit 10, which determines the oil-in-water content of the sample 3 from the first signal and the second signal. This concentration is determined by means of a calibration model, which combines the measured information about decay times at discrete wavelength intervals and about fluorescence intensities and determines the concentration therefrom. Additional information about the oil is given in the spectral distribution of the fluorescent light, its decay time, and its dependence upon the excitation wavelength. In one embodiment, further measurement values such as temperature, pressure, turbidity, absorption, pH, conductivity, density, dielectric constant, or others can also be considered.

Figure 2:
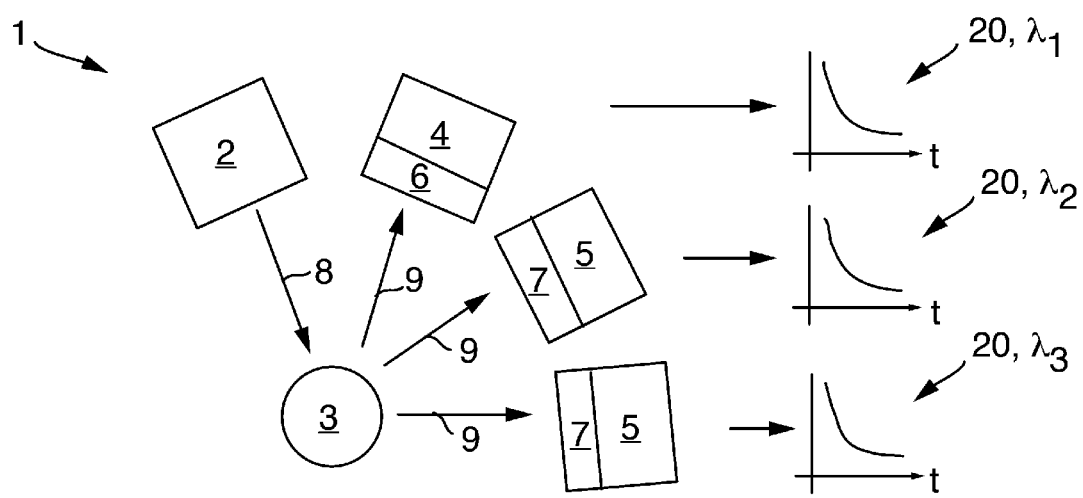
FIG. 2 shows the claimed optical measuring system in an embodiment.

In FIG. 2, the optical element is configured as a second photodiode 5. The first and second photodiodes 4, 5 each have a filter 6, 7 for a first or second wavelength interval $\lambda 1$, $\lambda 2$, wherein the second wavelength interval $\lambda 2$ differs from the first wavelength interval $\lambda 1$ at least in sections. The filters 6, 7 are designed as bandpass filters. In this way, a rough, i.e., consisting of only a few wavelength intervals $\lambda 1$, $\lambda 2$, time-resolved spectrum is achieved. A further photodiode 5 with a further filter 7, which in turn comprises a different wavelength range $\lambda 3$, is shown further as an embodiment. The oil-in-water concentration is determined on the basis of the decay curves 20 or the decay times at different wavelength ranges $\lambda 1$, $\lambda 2$, $\lambda 3$ by means of a calibration model. The data processing unit is not shown in FIGS. 2 and 3 but is the same as shown in FIG. 1.

Figure 3:
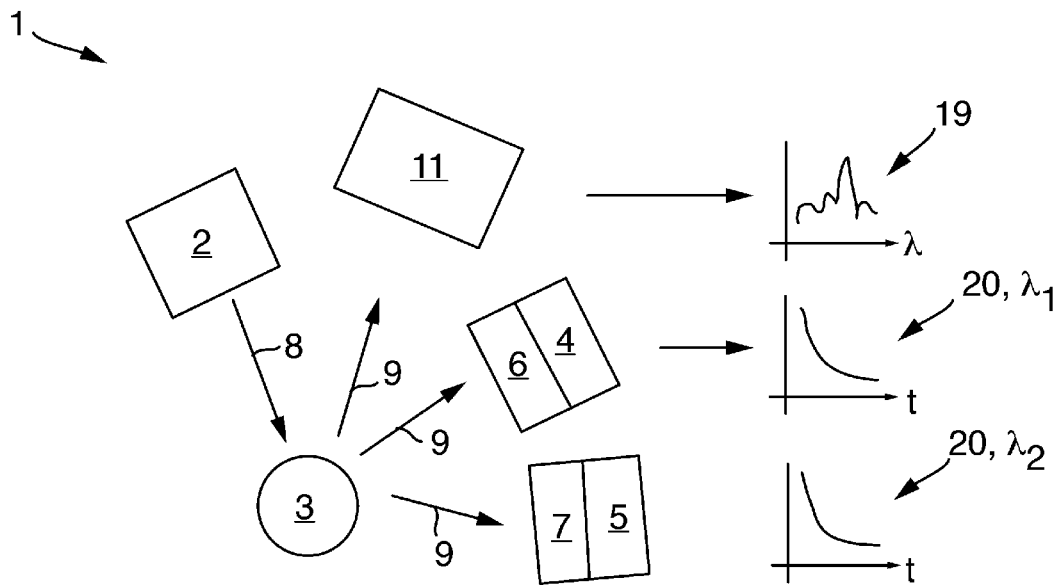
FIG. 3 shows the claimed optical measuring system in an embodiment.

FIG. 3 shows the combination of FIG. 1 with FIG. 2: a slow spectrometer 11 and several photodiodes 4, 5 with various, discrete bandpass filters 6, 7.

The structure of the measuring system 1 comprises one or more pulsed excitation light sources 2. For this purpose, LED's (for example, UV LED's), possibly of different wavelengths; a flash lamp (for example, a xenon flash lamp), possibly with different filters for excitation at different wavelengths; and lasers, possibly of different wavelengths, come into consideration. Optionally, the excitation light source includes a (its own) photodiode as a reference diode. Using this reference diode, the decay curve 20 can be determined at time t=0. This corresponds to the initial value. This reference diode also determines the decay curve 20 without medium. In one embodiment, the maximum peak is taken as a reference.

Figure 4:
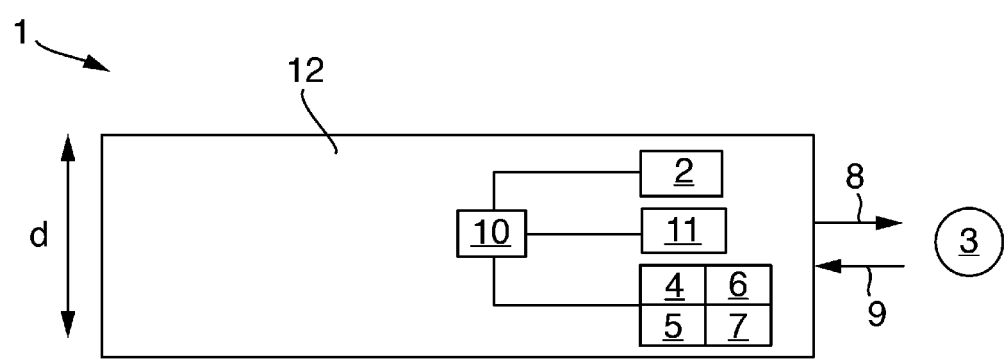
FIG. 4 shows a design of the claimed optical measuring system.

FIG. 4 shows a design of the optical measuring system 1. This is configured as immersion probe 12. Immersion probe 12 has a diameter d of 20-50 mm, e.g., 40 mm, wherein light source 2, first photodiode 4, optical component 5 (and/or 11), and data processing unit 10 are arranged in the immersion probe 12.

Figure 5:
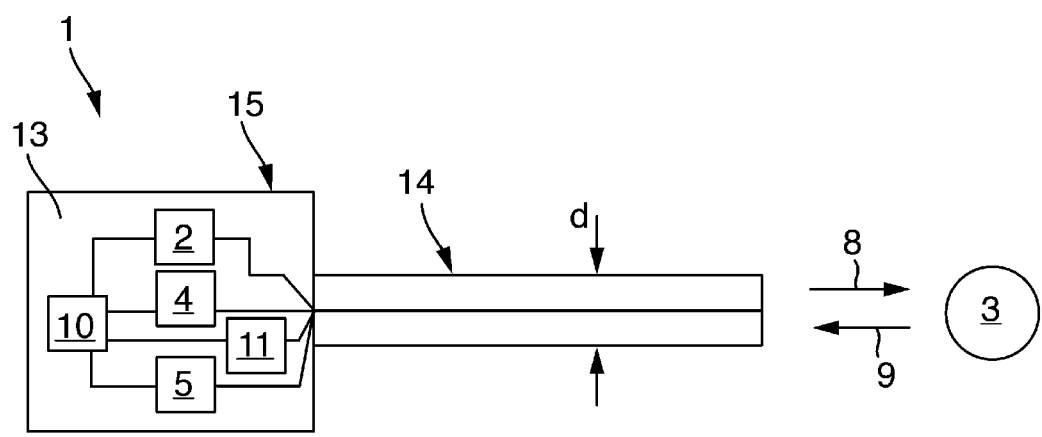
FIG. 5 shows a design in an embodiment of the claimed optical measuring system.

FIG. 5 shows a design of the optical measuring system 1. This is configured as immersion probe 13. The immersion probe 13 has a medium-contacting first section 14 with a diameter of about 12 mm and a non-medium-contacting second section 15 with a diameter greater than 12 mm, wherein light source 2, first photodiode 4, optical component 5 (and/or 11), and data processing unit 10 are arranged in the second section 15. The optical signals are guided from the second section 15 through the first section 14 in the direction of the medium 3 by means of, for example, optical light guides. The first section 14 is immersed in the medium 3.

Figure 6A:
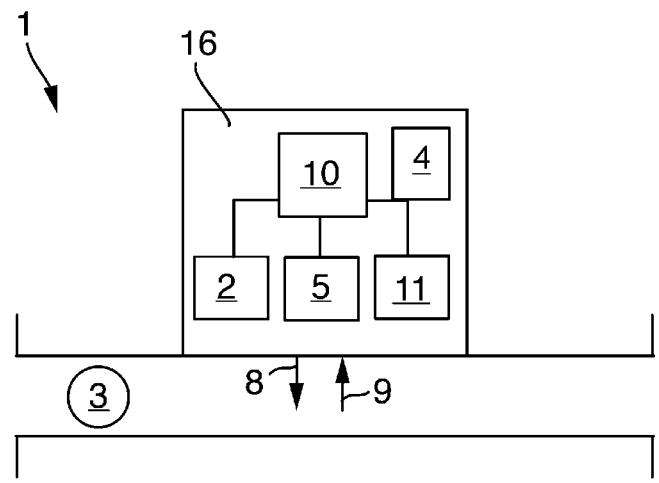
FIG. 6a/b shows a design in two embodiments of the claimed optical measuring system in cross-section.
Figure 6B:
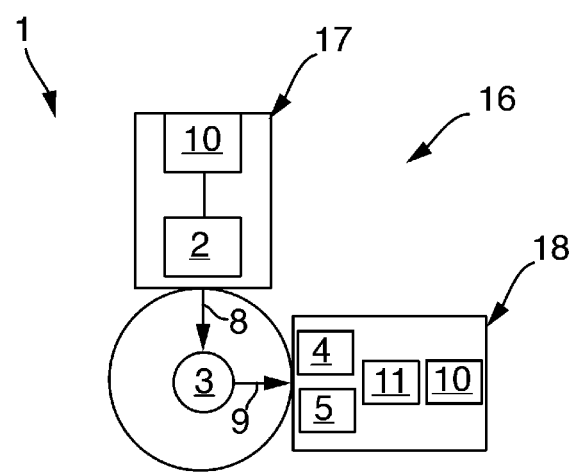

FIG. 6a/b shows a design of the optical measuring system 1. This is configured as a flow-through measuring cell 16. In FIG. 6a, the flow-through measuring cell 16 comprises a sensor head comprising the light source 2, first photodiode 4, optical component 5 (and/or 11), and data processing unit 10. In FIG. 6b, the light source 2 is arranged in a first module 17, and the first photodiode 4 and the optical component 5 (and/or 11) are arranged in a second module 18, wherein the first module 17 is offset from the second module 18. First and second modules 17, 18 either each comprise one data processing unit 10 or share one.

The embodiment in FIG. 6a/b and/or the other embodiments may thereby comprise a further filter. The further filter filters the exciting radiation. This makes it possible to prevent an amplifier from being overdriven. The further filter is designed as a high-pass filter or low-pass filter.

In one embodiment, the photodiode is not sensitive in the frequency range of the excitation light. In other words, a filter, in particular, the filters 6, 7, are not required.

The invention claimed is:

1. An optical measuring system, comprising:
    at least one light source radiating excitation light, in a UV/VIS wavelength range, into a medium to be measured, wherein the excitation light is converted by the medium into fluorescent light;
    a first photodiode configured to receive the fluorescent light and converting the fluorescent light into a first signal;
    at least one optical component configured to receive the fluorescent light and converting the fluorescent light into a second signal; and
    a data processing unit configured to generate a decay curve based on the first signal, wherein the decay curve includes a decay time of an intensity of or a phase shift of the fluorescent light over a period, the data processing unit further configured to determine an oil-in-water content based on the decay curve and the second signal.

2. The optical measuring system of claim 1, wherein the at least one optical component is configured as a second photodiode receiving the decay curve of the fluorescent light and converting it into the second signal.

3. The optical measuring system of claim 2, wherein the first photodiode includes a first filter for a first wavelength interval or wherein the second photodiode includes a second filter for a second wavelength interval, wherein the second wavelength interval differs from the first wavelength interval at least in sections.

4. The optical measuring system of claim 1, wherein the optical component is a spectrometer, wherein a time resolution of the spectrometer is insufficient for determining the decay curve of the fluorescent light.

5. The optical measuring system of claim 1, wherein the optical measuring system includes at least two optical components.

6. The optical measuring system of claim 1, wherein the light source is an LED, a flash lamp, or a laser.

7. The optical measuring system of claim 1, wherein the optical measuring system is an immersion probe having a diameter of 20-50 mm, wherein the light source, first photodiode, optical component, and data processing unit are positioned in the immersion probe.

8. An optical measuring system, comprising:
  at least one light source radiating excitation light into a medium to be measured, wherein the excitation light is converted by the medium into fluorescent light;
  a first photodiode receiving a decay curve of the fluorescent light and converting it into a first signal;
  at least one optical component receiving the fluorescent light and converting it into a second signal; and
  a data processing unit determining an oil-in-water content based on the first signal and the second signal;
  wherein the optical measuring system is an immersion probe including a medium contacting first section having a diameter of 12 mm and a non-medium-contacting second section having a diameter greater than or equal to 12 mm, wherein the light source, first photodiode, optical component, and data processing unit are positioned in the non-medium-contacting second section.

9. The optical measuring system of claim 1, wherein the optical measuring system is a flow-through measuring cell.

10. The optical measuring system of claim 1, wherein the light source is positioned in a first module, wherein the first photodiode and the optical component are positioned in a second module, and wherein the first module is offset from the second module.

11. A method for determining an oil-in-water content using an optical measuring system, the method comprising the steps of:
  radiating excitation light, in a UV/VIS wavelength range, into a medium to be measured, wherein the excitation light is converted into fluorescent light;
  measuring the fluorescent light over a period using a photodiode as to generate a decay curve of the fluorescent light;
  measuring the fluorescent light using an optical element; and
  determining the oil-in-water content using the measurements of the photodiode and the optical element.

* * * * *